United States Patent [19]

Green, II et al.

[11] Patent Number: 4,645,859

[45] Date of Patent: * Feb. 24, 1987

[54] METHODS FOR PURIFYING BIURET

[75] Inventors: James A. Green, II, Chino; Donald C. Young, Fullerton, both of Calif.

[73] Assignee: Union Oil Company of California, Los Angeles, Calif.

[*] Notice: The portion of the term of this patent subsequent to Feb. 24, 2004 has been disclaimed.

[21] Appl. No.: 725,304

[22] Filed: Apr. 19, 1985

Related U.S. Application Data

[63] Continuation-in-part of Ser. No. 567,271, Dec. 30, 1983, and a continuation-in-part of Ser. No. 567,099, Dec. 30, 1983, and a continuation-in-part of Ser. No. 567,047, Dec. 29, 1983.

[51] Int. Cl.$^4$ ............................................. C07C 126/08
[52] U.S. Cl. ......................................... 564/38; 564/73
[58] Field of Search .................................. 564/38, 73

[56] References Cited

U.S. PATENT DOCUMENTS

| | | | |
|---|---|---|---|
| 3,150,177 | 9/1964 | Kluge | 564/38 |
| 3,184,508 | 5/1965 | Kaasenbrood | 564/73 |
| 3,185,731 | 5/1965 | Kaasenbrood | 260/555 |
| 3,846,298 | 11/1974 | Plura | 210/33 |
| 3,903,158 | 9/1975 | Fuentes et al. | 260/555 |
| 4,345,099 | 8/1982 | Young et al. | 564/63 |

FOREIGN PATENT DOCUMENTS 1156099  6/1969  United Kingdom .

OTHER PUBLICATIONS

Redemann et al, Ind. and Eng. Chem., vol. 50, No. 4, (1958), pp. 633–636.
Takahashi & Yoshida, Determination of Biuret in Urea By Ion Exchange Resins, Soil and Plant Food, vol. 3, Jan. 1958, pp. 142–144.
Endo et al., Regeneration of Ion Exchange Columns, Chemical Abstract 90:143400z.
Donald C. Young and James A. Green, II, Application Ser. No. 567,271, filed Dec. 30, 1983, for Methods for Removing Biuret from Urea by Ion Exchange.
Donald C. Young and James A. Green, II, Application Ser. No. 567,099, filed Dec. 30, 1983, for Ion Exchange Methods for Removing Biuret from Urea.
Donald C. Young and James A. Green, II, Application Ser. No. 567,047, filed Dec. 30, 1983, for Method for Removing Biuret from Urea.
James A. Green II and Donald C. Young, U.S. application Ser. No. 732,175, filed May 7, 1985, for Manufacture of Biuret.

*Primary Examiner*—Charles F. Warren
*Assistant Examiner*—Elizabeth A. Flaherty
*Attorney, Agent, or Firm*—Michael H. Laird; Gregory F. Wirzbicki; Dean Sandford

[57] ABSTRACT

Methods are provided for recovering purified biuret from aqueous solutions containing biuret and higher molecular weight urea condensation products by contacting such solutions with the hydroxide ion form of an anion exchanger and extracting biuret from the ion exchanger with an aqueous extractant. The useful biuret-containing solutions also may contain urea. These methods are capable of recovering biuret of 99.9 percent plus purity from solutions containing higher molecular weight urea condensations products such as triuret, melamine, ammelide, and others. Elevated temperatures increase biuret recovery rate and concentration, and the extractant can be recycled into contact with additional biuret-containing anion exchangers to increase biuret concentration even further. The biuret-containing extract can be employed as is, concentrated by evaporation or otherwise, or treated to crystallize biuret. An integrated process is provided which involves pyrolyzing urea to form biuret and higher molecular weight condensation products and selectively recovering biuret from an aqueous solution of the resulting pyrolyzed urea as described.

31 Claims, No Drawings

METHODS FOR PURIFYING BIURET

RELATED APPLICATIONS

This application is a continuation-in-part of our co-pending applications Ser. No. 567,271, filed Dec. 30, 1983 for Methods For Removing Biuret From Urea by Ion Exchange, Ser. No. 567,099, filed Dec. 30, 1983 for Ion Exchange Methods For Removing Biuret From Urea, and Ser. No. 567,047, filed Dec. 29, 1983 for Methods For Removing Biuret From Urea.

BACKGROUND OF THE INVENTION

1. Field of the Invention

This invention relates to methods for producing biuret, and in particular, it relates to methods for recovering purified biuret from aqueous solutions which contain higher molecular weight urea condensation products.

2. Description of the Art

Biuret is widely used in commerce as a precursor for pharmaceuticals, herbicides, and other compounds, as an analytical reagent, and as a ruminant feed supplement. All of these utilities benefit from (if not require) the use of relatively pure biuret.

While biuret can be produced by several chemical methods, it is typically obtained by pyrolyzing urea at a temperature of at least 130° C. and for a period of time sufficient to convert at least a portion of the urea to biuret. An illustrative urea pyrolysis process is discussed by Shipley and Watchorn in British Pat. No. 1,156,099. Unfortunately, as disclosed by Shipley et al., a portion of the urea and biuret are often converted, during pyrolysis, to higher molecular weight urea condensation products such as triuret, cyanuric acid, ammelide, melamine, ammonium cyanurate, methylene diurea, and/or other compounds. Furthermore, a large part of the urea that is manufactured as solid prills is treated at temperatures, during the manufacturing process, that result in some conversion of urea to biuret and higher molecular weight compounds. While the biuret concentration in prilled ureas is typically low, e.g., 0.5 to 3 weight percent, the amount of biuret contained in such products is substantial due to the large volume of prilled urea manufactured annually. Many of the commercial biuret-containing prilled ureas also contain higher molecular weight urea condensation products such as those mentioned above.

Many of the higher molecular weight condensation products appear to form by the reaction of urea with itself or with previously formed condensation products, or by reactions of, or between, previously formed condensation products. Others, such as methylene diurea, appear to form by the reaction of urea and/or condensation products with additives or other impurities such as formaldehyde which is sometimes employed as a urea anti-caking agent. Regardless of their origin, one or more of such impurities are known to exist in biuret obtained from urea by presently available methods as discussed by Shipley et al., supra, and Kassenbrood in U.S. Pat. No. 3,185,731.

While urea pyrolysis and prilled urea manufacture afford an ample supply of biuret, the major utilities for biuret benefit from the use of that compound in relatively pure form. For instance, analytical procedures and pharmaceutical and herbicide manufacturing practices involving the use of biuret are most often unacceptably complicated by the presence of higher molecular weight condensation products, and the biuret dosage rate which can be employed in ruminant feed supplements is often limited by the toxicity of such impurities.

Methods presently employed to recover pure biuret from mixtures of urea, biuret and higher molecular weight condensation products involve expensive, time consuming, repeated low temperature recrystallization from aqueous solution. The expense involved in such methods obviously increases the cost of pure biuret derived from such sources and limits its application. For instance, ruminant feed supplement manufacturers generally choose to use relatively impure, less expensive biuret at dosage rates which are sufficiently low to avoid the toxic effects of impurities.

While several authors have disclosed that biuret can be removed from urea by contact with the hydroxide ion form of an anion exchanger, they have not recognized that impurity-free biuret can be efficiently recovered from aqueous solutions containing higher molecular weight urea condensation products. For instance Fuentes et al., U.S. Pat. No. 3,903,158 and Takahashi et al., "Determination of Biuret in Urea by Ion Exchange Resins," Soil and Plant Food, Volume 3, No. 3, January 1958, pages 142–144, disclose that biuret can be removed from aqueous solutions by ion exchange. However, neither Fuentes et al. nor Takahashi et al. mention the presence of any other impurities or the possibility that impurity-free biuret can be recovered from solutions containing higher molecular weight urea condensation products. In fact, Takahashi et al. disclose that "usually, urea for agriculture does not contain nitrogen compounds other than biuret." (Ibid., page 144). While that is often the case, some urea solutions, and in particular those which are formed from urea which has been subjected to pyrolysis at temperatures above 130° C. for any significant period of time, contain a significant proportion of urea condensation products of higher molecular weight than biuret, some of which are toxic, and all of which can impair product utility.

SUMMARY OF THE INVENTION

It has now been discovered that biuret can be selectively, efficiently and economically recovered from aqueous solutions containing biuret and higher molecular weight urea condensation products by contacting such solutions with ion exchangers. More specifically, in the present procedure purified biuret is produced by contacting aqueous solutions containing biuret and higher molecular weight urea condensation products with the hydroxide ion form of an anion exchanger under conditions sufficient to retain at least a portion of the biuret on the anion exchanger, and extracting at least a portion of the retained biuret from the anion exchanger with an aqueous extractant under conditions sufficient to obtain a biuret-containing extract which contains a lower relative proportion of the higher molecular weight urea condensation products. The preferred method of the invention further provides for the relatively selective recovery of biuret from aqueous solutions which contain substantial amounts of urea.

While the extractant can be either acidic, neutral or alkaline, highly alkaline extractants are desirably neutralized and/or cooled prior to extraction to minimize or eliminate biuret loss by hydrolysis. Extracts which have higher biuret concentrations can be obtained by performing the extraction at elevated temperatures, e.g. of at least about 30° C., and/or by recycling the biuret-containing extract into contact with one or more biuret-containing anion exchangers. Pure biuret can be obtained by chilling the extract to a temperature sufficient to crystallize biuret from the solution.

These methods provide for the efficient and economical recovery of biuret from aqueous solutions containing biuret and higher molecular weight urea condensation products without the expense or complexity of repeated, low temperature recrystallization (which is otherwise required to separate biuret from higher molecular weight urea condensation products). While the fate of the higher molecular weight impurities is not known with certainty, one or more of such impurities may be decomposed by contact with the anion exchanger while others may pass through the exchanger ahead of the biuret. Whatever the exact chemical mechansim, the methods of this invention can be employed to recover biuret of purity as high as 99.9 plus weight percent from aqueous solutions which contain biuret and higher molecular weight urea condensation products in the presence or absence of urea. These methods have the further advantage that they enable the recovery of purified biuret as a by-product of urea purification as described in our above identified co-pending applications, Ser. Nos. 567,271, 567,099, and 567,047, the disclosures of which are incorporated herein by reference in their entireties. They also enable the essentially complete recovery of purified biuret from such impurity-containing solutions without significant biuret loss due to hydrolysis or other chemical reactions.

DETAILED DESCRIPTION OF THE INVENTION

One embodiment of this invention involves selectively removing biuret from aqueous solutions which contain biuret and higher molecular weight urea condensation products, in the presence or absence of urea, by contacting such aqueous solutions with the hydroxide ion form of an anion exchanger under conditions sufficient to retain at least a portion of the biuret on the exchanger and subsequentially removing the retained biuret by contact with an aqueous extractant. Although acidic, neutral and alkaline extractants can be employed, the alkaline extractants are preferably neutralized to about pH 7 or less following the biuret extraction step to prevent biuret hydrolysis.

These procedures are capable of producing biuret of 99.9 percent plus purity from aqueous solutions which contain substantial proportions of higher molecular weight urea condensation products such as triuret, melamine, etc. Biuret concentration in the extract can be increased by employing higher extraction temperatures, e.g. 30° C. or higher, and/or by recycling the biuret-containing extract into contact with one or more biuret-containing exchangers to extract additional biuret. The biuret-containing extract can be employed as is, can be concentrated further by evaporation, or can be employed to produce pure, solid biuret by low temperature crystallization.

Another embodiment provides an integrated process for producing biuret from urea in which urea is pyrolyzed at a temperature of about 130° C. or higher and for a period of time sufficient to convert at least a portion of the urea to biuret and higher molecular weight urea condensation products, after which the urea, biuret and impurities are dissolved in water and biuret is recovered as described above. When all of the urea has not been pyrolyzed, residual urea solution of reduced biuret content can be recovered and employed to produce additional quantities of biuret by pyrolysis.

The aqueous biuret-containing solutions useful in this invention include solutions which also contain higher molecular weight urea condensation products, such as triuret, cyanuric acid, ammonium cyanurate, methylene diurea, and cyclic polyamides such as melamine and ammelide. Such solutions can either be employed as manufactured commercially or they can be pretreated (by exposure to elevated temperatures) to increase biuret content. Broadly speaking, the useful solutions include those obtained from urea manufacturing plants prior to dehydration, solutions formed by dissolving impure biuret or biuret-containing urea in water, and impure biuret solutions from which some or all of the urea has been separated by crystallization or otherwise as discussed, for instance in British Pat. No. 1,156,099 and U.S. Pat. No. 3,185,731, the disclosures of which are incorporated herein by reference in their entireties.

Many commercially available prilled ureas, which are typically formed by prilling urea from a melt at a temperature of about 130° C. or higher, contain about 0.5 to about 3 weight percent biuret based on urea in addition to higher molecular weight condensation products. The impurities constitute at least about 5, generally at least about 10 and most often about 5 to about 50 weight percent of the composition based on biuret. Triuret usually accounts for approximately one half of the impurity content of impure prilled urea.

Ureas which have been intentionally pyrolyzed to form biuret typically contain substantially higher proportions of biuret and higher molecular weight impurities. Pyrolysis is usually effected by treatment at a temperature of at least about 135° C., generally about 135° to about 180° C., for a period of time sufficient to convert at least a portion of the urea to biuret. Contact times of at least about 2 minutes are usually employed, although significant urea conversion usually requires treatment for about 5 minutes to about 5 hours. The rate of urea conversion increases with temperature; thus, the contact time required to achieve a certain degree of urea pyrolysis decreases as treatment temperature is increased.

While all of the urea can be pyrolyzed to biuret and higher molecular weight urea condensation products, higher conversions require the use of higher temperatures and/or longer contact times which result in higher impurity/biuret ratios and the loss of biuret product. Biuret loss under severe pyrolysis conditions is due, at least in part, to the pyrolysis of biuret to higher molecular weight compounds. Thus, the urea is typically only partially pyrolyzed under conditions sufficient to yield at least about 5 weight percent, generally about 10 to about 50 weight percent biuret based on urea. The higher biuret concentrations are usually associated with higher impurity/biuret ratios due to the more severe pyrolysis required to achieve such biuret levels. Further explanation of the relationship of pyrolysis time and temperature and of impurity concentration is given in "Urea, Its Properties and Manufacture," George C. Tsei-Yu-Chao, 1967, Library of Congress Catalog Card number Ai-11254, published by Chao's Institute, West Covina, Calif. particularly on pages 119-123, the disclosure of which is incorporated herein by reference.

Thus, rather than aiming to form pure biuret by pyrolysis of urea, the present invention seeks to selectively recover essentially pure biuret from aqueous solutions containing biuret and higher molecular weight urea condensation products. Typically, such solutions contain about 1 to about 80 weight percent, preferably about 2 to about 70 weight percent solute including biuret and higher molecular weight urea condensation products in the presence or absence of urea. Maximum solution concentration is usually determined by solution temperature which can range from 10° C. to about 100° C. However, at temperatures above 70° C. urea decomposition by hydrolysis becomes more rapid. Accordingly, aqueous solutions which contain substantial urea are preferably maintained at about 70° C. or less.

Urea has a solubility of approximately 80 weight percent in water at 70° C. and biuret will dissolve in water to a level of approximately 20 weight percent at the same temperature. However, biuret is more soluble in urea solutions. Thus, higher biuret concentrations can be achieved in the presence of substantial amounts of dissolved urea.

While the aqueous solutions can be employed as prepared, they usually contain sufficient ammonia to produce a relatively basic aqueous solution. Although this condition can be tolerated, pH levels of about 12 and above promote urea and biuret hydrolysis and are preferably avoided. Accordingly, the aqueous feed solutions will usually be relatively non-alkaline and will generally have a pH below 12, usually about 10 or less, preferably about 6 or less, and most preferably about 3 to about 6. Alkaline solutions can be neutralized and/or buffered to obtain the desired pH by adding any suitable organic or inorganic acid such as sulfuric, hydrochloric, nitric, acetic, etc., or buffering agents such as ammonium polyphosphate. Relatively acidic solutions are particularly preferred for use at higher temperatures and/or longer contact times.

The anion exchangers useful in the present invention can be either organic or inorganic, basic ion exchangers or combinations of organic and inorganic anion exchangers. The anion exchanger is preferably at least moderately basic and is most preferably a strongly basic anion exchanger such as those marketed by Rohm & Haas Company under the trademarks Amberlite IRA-400, IRA-458, and IRA-900, and the like, by the Dow Chemical Company under the Trademark Dowex I-X4, and by the BIORad Company under the trademark AG MP-1, and others.

The presently preferred anion exchangers are the strongly basic, organic ion exchange resins which contain tertiary and/or quaternary amine groups. Such anion exchangers can be prepared by the chloromethylation of a styrene-divinylbenzene copolymer which is then reacted with a tertiary or secondary amine, by the condensation of phenylenediamine with formaldehyde, or by the condensation of phenylenediamine, polyethyleneimine and formaldehyde. Particularly preferred anion exchangers are the quaternary amine types such as those disclosed in U.S. Pat. No. 2,591,573, the disclosure of which is incorporated herein by reference in its entirety.

The hydroxide ion form of the anion exchangers is presently preferred to effect the selective removal of biuret from the biuret-containing solutions. However, many of the commercially available anion exchangers are manufactured and sold in other ionic forms, such as the chloride form, and require conversion to the hydroxide form prior to use. Such conversion can be readily accomplished by contacting the exchanger with an aqueous solution of a strong base as described, for instance, in "Ion Exchange with the Amberlite Resins" and "Amberlite IRA-400—Laboratory Manual," both of which are available from the Resinous Products Division, Rohm & Haas Company, Washington Square, Philadelphia, Pa., and both of which are incorporated herein by reference in their entireties. Suitable procedures for converting the chloride ion form of anion exchangers to the preferred hydroxide ion form and for regenerating anion exchangers are also discussed in our above noted co-pending applications.

All of the process steps, including the extraction of biuret from the feed solution and the removal of biuret from the resulting biuret-containing anion exchanger, can be performed either by batch contacting or by continuous plug flow contacting in which the feed, extractant and regenerant solutions are passed through the anion exchanger retained in a relatively fixed bed. Plug flow systems can be operated either downflow or upflow, although downflow systems are generally preferred.

Each increment of the biuret-containing feed solution is usually contacted with the anion exchanger for at least about 30 seconds, preferably at least about one minute, most preferably at least about 5 minutes, and generally about one minute to about one hour. Contact times of about 5 to about 30 minutes are usually adequate to effect the desired degree of biuret removal. Such contact times correspond to flow rates of about 2 bed volumes per minute or less, usually about 1 bed volume per minute or less, preferably about 0.2 bed volumes per minute or less, and most preferably about 0.02 to about 1 bed volume per minute.

Contact of the anion exchanger with the biuret-containing feed is usually, although not necessarily, continued until the capacity of the anion exchanger is depleted. Depletion of exchanger capacity is indicated in the preferred, continuous, fixed bed systems by biuret breakthrough, which occurs when a detectable quantity of biuret is present in the solution recovered from the anion exchanger. However, the biuret exchange step can be continued past the point of biuret breakthrough if desired.

After completion of the biuret extraction step, the feed solution remaining in contact with the anion exchanger can be recovered and either returned to the feed solution reservoir, to a product accumulator, or otherwise as desired.

It is sometimes desirable, although not essential, to backwash the resin to remove foreign matter, to flush remaining feed solution from the anion exchanger, and/or to "reclassify" the bed of anion exchanger particles. Backwashing is usually effected by passing water rapidly upwardly through the bed to expand the bed by, e.g., 50 percent. However, substantial backwashing of the biuret-containing exchanger at this point in the operation is not preferred since, as discussed in our above noted co-pending applications, even neutral water is capable of removing biuret from the exchanger. Thus, biuret recovery can be maximized by deferring substantial backwashing until the biuret recovery step is completed as described hereinafter. However, the exchanger can be washed with a minor amount of water, e.g. one bed volume or less, and/or can be blown free of residual feed solution with a pressurized gas such as air, nitrogen, etc., to reduce or prevent contamination of the biuret product with the feed and other impurities.

The biuret-containing solution can be contacted with the anion exchanger at any temperature above the freezing point of the solution and below the upper temperature limit of the anion exchanger. Typically, the solution will be contacted with the exchanger at a temperature of about 0° to about 100° C., generally about 25° to about 70° C. and preferably about 30° to 70° C. While higher temperatures can be employed, urea decomposition rate (to $CO_2$ and ammonia) increases rapidly at temperatures above 70° C., and such temperatures are preferably avoided. Higher temperatures increase solubility and biuret exchange rate and thereby reduce the time required to achieve a given degree of biuret exchange. They also markedly increase urea and biuret hydrolysis rates under alkaline conditions. Therefore, it is preferable to acidify the feed solution at least to about neutrality and preferably to a pH below 7 when higher solution contacting temperatures are employed.

After the biuret exchange step, excess feed solution is removed from the exchanger, and the biuret-containing exchanger is contacted with an aqueous extractant under conditions sufficient to form an aqueous biuret-containing extract substantially free of higher molecular weight urea condensation products. The aqueous extractant can be contacted with the exchanger by either batch or column operations as described above with regard to the biuret exchange operation.

The aqueous extractant can be either acidic, neutral or alkaline, although substantially non-alkaline extractants are presently preferred due to the tendency of alkaline media to hydrolyze biuret, particularly at elevated temperatures. Illustrative extractants include water, ammonium hydroxide solution, e.g. (1N $NH_4OH$), and caustic, e.g., up to 8 percent sodium hydroxide. Calcium-free and carbonate-free, substantially nonalkaline extractants are presently preferred since alkaline materials promote biuret hydrolysis while calcium and carbonate ions impair the exchanger regenerability for subsequent extraction of biuret from the feed solutions. Thus, deionized water or distilled water are presently preferred, and these can be acidified if desired.

At least slight acidification of the extractant, either before contacting with the exchanger or subsequent to the biuret removal step, is presently preferred, particularly when operating at higher temperatures. Acidification minimizes the loss of biuret by hydrolysis. Thus, the most preferred extractants usually have a pH of about 7 or less, preferably below about 6, and generally within the range of about 1 to about 7. Any organic or inorganic acid can be employed to effect the desired degree of acidification.

When alkaline extractants are employed, contacting temperature is preferably maintained below about 25° C., most preferably about 20° C. or less, and the extract is preferably neutralized with acid to approximately pH neutral or acidic conditions within a short time after its removal from contact with the exchanger.

The biuret-containing exchanger is contacted with a sufficient volume of extractant for a sufficient period of time to remove a substantial proportion of the biuret from the exchanger. Typically, at least one volume of extractant will be employed per volume of exchanger although much higher extractant volumes can be used. Thus, extractant volume will usually range from about 1 to about 100 volumes per volume of exchanger, although most operations will involve the use of about 1 to about 10 volumes of extractant per volume of exchanger. Shorter contact times are required to achieve the same degree of biuret removal at higher temperatures due to increased biuret solubility and high desorption rates. Thus, contact time can be varied depending on the temperature employed. Typically, contact times for the extraction step will be at least about 10 minutes to about 5 hours. Such contact times, in fixed bed systems, correspond to extractant flow rates of less than about 10, preferably less than about 5 volumes of extract per volume of exchanger per hour (V/V/hr.).

Extraction temperature should be sufficiently low to prevent substantial biuret hydrolysis, particularly when alkaline extractants are employed. Thus, extraction temperatures are generally below 40° C. and preferably below 30° C. when basic extractants are used. Biuret hydrolysis in alkaline systems is relatively slow at 24° C.

Neutral or acidic extractants can be employed at higher temperatures without significant biuret hydrolysis, and higher temperatures are presently preferred due to the higher solubility of biuret at such temperatures. For instance, biuret solubility in pure water is 0.53 weight percent at 0° C., 2 percent at 25° C., 7 percent at 50° C., 20 percent at 75° C., and almost 48 percent at 100° C. Elevated temperatures also increase biuret desorption rate from the exchanger. Accordingly, neutral or acidic extractants and elevated temperatures of at least about 25° C., generally about 25° to about 100° C., and preferably about 30° to about 100° C. are presently employed.

Extractant-exchanger contacting can be by either batch or co-current or countercurrent fixed bed procedures or combinations of these. Furthermore, single or multiple contacts with the same or different extractant can be employed in both batch and fixed bed systems. In a presently preferred embodiment, the extract recovered from the exchanger is recycled into contact either with the same ion exchanger or with another biuret-containing ion exchanger to increase the biuret concentration in the extract. Also, the first portion of extract (a fraction of an exchanger volume up to several volumes) recovered from the exchanger, which typically has a higher biuret content than subsequent portions of extract, can be recovered as product and/or processed by crystallization, evaporation, etc., and subsequent portions, typically of lower biuret content, can be recycled.

The extractant can be recycled up to 100 times depending on the biuret concentration desired, contact time between each volume of extractant during each cycle, temperature, and the quantity of biuret on each exchanger contacted. Usually, however, the extractant, or a portion thereof, will be recycled 1 to about 20 times unless biuret is recovered from the extractant. If biuret is removed by crystallization or otherwise, the extractant can be recycled indefinitely.

It is sometimes preferable to obtain an extract having a relatively high biuret content, e.g. of 4 weight percent or more, for instance when biuret is to be recovered from the extract by crystallization or otherwise. Such high biuret concentrations can be achieved by the use of longer contact times, lower volumes of extractant per volume of exchanger, higher exchanger biuret loadings, higher contacting temperatures, higher recycle ratios or combinations of two or more of these procedures.

The recovered biuret-containing extract will generally contain at least about 0.1 weight percent, typically about 0.1 to about 50 weight percent, and preferably about 2 to about 50 weight percent biuret. Biuret concentrations of at least about 4 weight percent, particularly at least about 10 weight percent, are preferred for the production of more concentrated solutions, e.g. by evaporation, or for the production of solid biuret by crystallization or otherwise.

Following recovery of the biuret-containing extract from the ion exchanger, the exchanger can be employed to remove biuret from additional quantities of the impure biuret-containing feed solution with or without further regeneration. As discussed in our above referenced copending applications, the useful ion exchangers can be regenerated by contact with water. However, the useful ion exchangers can lose a significant portion of their activity after multiple regenerations with only water and, in such instances, regeneration with caustic and/or acid is presently preferred. Regeneration with strong caustic, e.g. 2 to about 8 weight percent sodium hydroxide solution, is usually sufficient to restore most if not all of the anion exchanger activity. On occasion, however, the accumulation of impurities on the ion exchanger makes it desirable to regenerate with acids such as hydrochloric acid followed by reconversion of the ion exchanger to the useful hydroxide-ion form. Procedures suitable for effecting such regeneration are discussed in our above referenced copending applications.

Extracts prepared in accordance with this invention are substantially free of the higher molecular weight urea condensation products present in the feed. Typically, the proportion of higher molecular weight impurities present in the extract will be less than one half, preferably less than one tenth the concentration of those impurities in the feed solution based on biuret. Thus, biuret of greater than 95 percent purity can be obtained by these methods. When care is taken to avoid contamination of the extract with the residual feed solution on the ion exchanger, biuret purity of at least about 99 percent and even 99.9 percent plus can be achieved.

The recovered biuret-containing extract can be employed as is as a herbicide, chemical precursor, animal feed supplement, or for other utilities. Alternatively, a proportion or all of the water in the extract can be evaporated to obtain either crystalline biuret or a concentrated biuret solution. When elevated temperature evaporation is employed, care should be taken to assure that the extract is approximately pH neutral or acidic prior to exposure to elevated temperatures to avoid biuret loss.

In a particularly preferred embodiment, the biuret concentration in the extract is increased either by recycling or otherwise as described above or by evaporation to obtain a biuret concentration of at least about 4 weight percent, preferably at least about 10 weight percent biuret, after which the concentrated solution is chilled to a temperature, e.g. about 0° C., sufficient to crystallize biuret from the solution. The crystalline biuret can be recovered by any suitable solid-liquid separation means such as filtration, decanting, etc.

The invention is further described by the following examples which are illustrative of specific modes of practicing the invention and are not intended as limiting the scope of the invention as defined by the appended claims.

EXAMPLE 1

An aqueous solution containing approximately 50 weight percent urea, 1.9 weight percent biuret based on urea and a variety of higher molecular weight urea condensation products including methylene diurea and triuret was passed downwardly at a rate of 25 ml./min. through a glass ion exchange column packed with 250 ml. of the hydroxide ion form of BIORAD ® AG-MP1 at a temperature of approximately 25° C. until biuret was detected in the column effluent. Urea solution feed to the column was then discontinued.

The concentration of urea, biuret, and higher molecular weight urea condensation products in the urea feed solution and urea effluent from the ion exchange column were determined by liquid chromatographic analyses which demonstrated that the majority of the higher molecular weight urea condensation products had been removed from the biuret in the column effluent leaving purified biuret on the ion exchange resin. The purified biuret can be removed from the ion exchange resin by contacting the resin with water or alkaline or acidic solutions.

EXAMPLE 2

The aqueous urea feed solution described in Example 1 was passed downwardly through a 200 ml. bed of the hydroxide ion form of Rohm and Haas basic anion exchange resin IRA-458 at a rate of 60 ml./min. until biuret was detected in the column effluent. Urea feed solution flow was then discontinued, residual urea feed solution was removed from the ion exchange resin, and the resin was washed with 20 bed volumes of deionized water passed downwardly over the ion exchanger at a rate of 60 ml. per minute. This treatment was sufficient to recover approximately 76 percent of the purified biuret from the anion exchanger. Maximum biuret concentration in the deionized water extract was approximately 0.5 weight percent which occurred in the first 2.5 bed volumes of deionized water extractant. Biuret concentration in subsequent portions of the extract gradually declined from that maximum level.

EXAMPLE 3

The urea feed solution described in Example 1 was passed downwardly over a 29 ml. bed of the hydroxide ion form of Rohm and Haas anion exchange resin IRA-400 at a rate of 9 ml./min. (0.3 bed volumes per minute) until biuret appeared in the column effluent. Urea solution feed was then discontinued, residual urea feed solution was removed from the anion exchanger, and purified biuret was recovered from the anion exchanger by passing 11.8 bed volumes of a 4 weight percent sodium hydroxide solution in deionized water downwardly through the column at approximately 9 ml./min. This treatment was sufficient to recover approximately 90 percent of the purified biuret from the exchanger.

EXAMPLE 4

The aqueous urea solution described in Example 1 was passed downwardly through a 250 ml. bed of the hydroxide form of Rohm and Haas IRA-458 ion exchange resin at a rate of 0.3 bed volumes per minute until biuret was detected in the exchanger effluent. Urea feed to the column was then discontinued, residual urea feed solution was removed from the anion exchanger, and purified biuret was then extracted from the anion exchanger by passing downwardly through the column 10 bed volumes of a 4 weight percent sodium hydroxide solution in deionized water. The sodium hydroxide extractant was withdrawn from and recycled to an extractant reservoir having an initial total volume of 10 bed volumes (2500 ml.).

The described biuret exchange and extraction steps were repeated seven additional cycles for a total of eight cycles. In each cycle, the same 10 volumes of sodium hydroxide extractant were employed to remove additional quantities of biuret from the anion exchanger.

After five cycles, the biuret concentration in the sodium hydroxide extractant had reached 0.68 weight percent. Biuret concentration in the sodium hydroxide extractant increased to 1.1 weight percent by the end of the eighth cycle.

This operation demonstrates that the concentration of purified biuret in extracts can be increased by recycling the extract into contact with biuret-containing anion exchangers.

EXAMPLE 5

This Example illustrates one procedure by which the concentration of purified biuret in a non-alkaline extract can be increased by recycling the biuret-containing extract into contact with biuret-containing anion exchangers.

Purified biuret can be recovered from an aqueous solution containing 40 weight percent urea, 3 weight percent biuret based on urea, and 10 weight percent higher molecular weight urea condensation products based on biuret, by passing the solution downwardly over a packed bed of the hydroxide ion form of Rohm and Haas IRA-458 basic anion exchanger at a rate of 0.3 bed volumes per minute and a temperature of 40° C. until a substantial portion of biuret has been removed from the solution and retained on the resin. Urea feed solution flow is then discontinued, residual urea feed solution is removed from the anion exchange column and biuret is recovered from the anion exchanger by contact with 20 bed volumes of deionized water passed downwardly over the exchanger at a rate of 0.3 bed volumes per minute. The described biuret exchange and extraction steps can be repeated five times employing the same 20 bed volumes of deionized water extractant in each extraction step to obtain an extractant containing more than 0.5 weight percent biuret which is at least 95 percent pure biuret, i.e. which contains less than 5 weight percent higher molecular weight urea condensation products based on biuret.

While particular embodiments of this invention have been described, it will be understood, of course, that the invention is not limited thereto since many obvious modifications can be made, and it is intended to include within this invention any such modifications as will fall within the spirit and scope of the appended claims.

We claim:

1. A method for recovering purified biuret from an aqueous solution containing biuret and higher molecular weight urea condensation products which comprises (a) contacting said aqueous solution with the hydroxide ion form of an anion exchanger under conditions sufficient to retain at least a portion of said biuret on said anion exchanger and (b) contacting the resulting biuret-containing anion exchanger with an aqueous extractant under conditions sufficient to form a biuret-containing aqueous extract in which the relative proportion of said higher molecular weight urea condensation products to biuret is less than said relative proportion in said aqueous solution.

2. The method defined in claim 1 wherein said higher molecular weight urea condensation products comprise a member selected from the group consisting of triuret, melamine, cyanuric acid, ammonium cyanurate, ammelide, methylene diurea, and combinations thereof, and said higher molecular weight urea condensation products constitute less than 5 weight percent of said extract based on biuret.

3. The method defined in claim 2 wherein said higher molecular weight urea condensation products comprise about one weight percent or less of said extract based on biuret.

4. The method defined in claim 1 which further comprises the step of contacting said biuret-containing extract with a biuret-containing anion exchanger under conditions sufficient to increase the biuret concentration of said extract.

5. The method defined in claim 1 wherein said aqueous extractant contacted with said biuret-containing anion exchanger has a pH below about 7.

6. The method defined in claim 5 wherein said pH is below about 6.

7. The method defined in claim 1 which further comprises the step of reducing the pH of said biuret-containing extract to less than 7.

8. The method defined in claim 1 wherein said aqueous extractant is contacted with said biuret-containing anion exchanger at a temperature of at least about 30° C.

9. The method defined in claim 1 wherein said aqueous extractant is contacted with said biuret-containing anion exchanger at a temperature of at least about 50° C.

10. The method defined in claim 1 wherein said aqueous extractant has a pH below 7 and is contacted with said biuret-containing anion exchanger at a temperature of at least about 30° C.

11. The method defined in claim 1 wherein said higher molecular weight urea condensation products comprise a member selected from the group consisting of triuret, melamine, cyanuric acid, ammonium cyanurate, ammelide, methylene diurea and combinations thereof, said aqueous extractant has a pH below 7 and is contacted with said biuret-containing anion exchanger at a temperature of at least about 50° C., and said higher molecular weight condensation products constitute about 5 weight percent or less of said biuret-containing extract.

12. The method defined in claim 11 wherein at least a portion of said biuret is recovered from said extract.

13. The method defined in claim 11 wherein said biuret-containing extract is cooled to a temperature sufficient to crystallize at least a portion of said biuret from said extract.

14. The method defined in claim 1 wherein said aqueous solution comprises at least about 5 weight percent urea, at least about 1 weight percent biuret based on urea, and at least about 10 weight percent of said higher molecular weight urea condensation products based on biuret.

15. The method defined in claim 1 wherein said aqueous urea solution comprises at least about 5 weight percent biuret.

16. The method defined in claim 1 wherein said aqueous solution comprises at least about 10 weight percent urea and at least about 10 weight percent biuret based on said urea, and said solution is prepared, at least in part, by heating urea at a temperature of at least about 135° C. for a period of time sufficient to pyrolyze at least a portion of said urea to biuret.

17. A method for selectively recovering biuret from an aqueous urea solution containing biuret and higher molecular weight urea condensation products which comprises contacting said solution with the hydroxide ion form of an anion exchanger under conditions sufficient to retain at least a portion of said biuret on said anion exchanger, and contacting the resulting biuret-containing anion exchanger with an aqueous extractant under conditions sufficient to remove at least a portion of said biuret from said anion exchanger and form an extract in which the relative proportion of said higher molecular weight urea condensation products to biuret is less than said relative proportion in said aqueous urea solution.

18. The method defined in claim 17 wherein said higher molecular urea condensation products comprise a member selected from the group consisting of triuret, melamine, cyanuric acid, ammonium cyanurate, ammelide, methylene diurea and combinations thereof, and the resulting biuret-containing extract is substantially free of said higher molecular weight condensation products.

19. A method for selectively recovering biuret from an aqueous urea solution containing biuret and higher molecular weight urea condensation products selected from the group consisting of triuret, melamine, cyanuric acid, ammonium cyanurate, ammelide, methylene diurea and combinations thereof, which method comprises contacting said urea solution with the hydroxide ion form of an anion exchanger under conditions sufficient to retain at least a portion of said biuret on said anion exchanger, and contacting the resulting biuret-containing anion exchanger with an aqueous extractant under conditions sufficient to form an aqueous extract comprising biuret in which the relative proportion of said higher molecular weight condensation products to biuret is less than said relative proportion in said aqueous urea solution.

20. The method defined in claim 19 wherein said aqueous urea solution comprises at least about 10 weight percent urea, at least about one weight percent biuret based on urea, and at least about 10 weight percent of said higher molecular weight condensation products based on biuret, and said aqueous extract contains about 5 weight percent or less of said higher molecular weight condensation products based on biuret.

21. A method for recovering biuret from an aqueous solution containing urea, biuret and a member selected from the aqueous consisting of triuret, melamine, cyanuric acid, ammonium cyanurate, ammelide, methylene diurea and combinations thereof, which comprises contacting said aqueous solution with the hydroxide ion form of an anion exchanger under conditions sufficient to retain at least a portion of said biuret on said anion exchanger, and contacting the resulting biuret-containing ion exchanger with an aqueous extractant having a pH of about 6 or less at a temperature of at least about 30° C. and under conditions sufficient to extract at least a portion of said biuret from said ion exchanger and form an extract in which the relative proportion of said higher molecular weight urea condensation products to biuret is less than said relative proportion in said aqueous solution.

22. The method defined in claim 21 wherein said aqueous extractant is contacted with said biuret-containing anion exchanger a temperature of at least about 50° C. and under conditions sufficient to produce an extract containing at least about one weight percent biuret.

23. A method for selectively recovering biuret from an aqueous solution comprising biuret and a member selected from the group consisting of triuret, melamine, cyanuric acid, ammonium cyanurate, ammelide, methylene diurea and combinations thereof, which comprises contacting an aqueous solution with the hydroxide ion form of an anion exchanger under conditions sufficient to retain at least a portion of said biuret on said ion exchanger, contacting the thus formed biuret-containing anion exchanger with an aqueous extractant under conditions sufficient to extract at least a portion of said biuret from said anion exchanger and form a biuret-containing extract in which the relative proportion of said higher molecular weight urea condensation products to biuret is less than said relative proportion in said aqueous solution, recovering said biuret-containing extract from said anion exchanger, and subsequently contacting said biuret-containing extract with a biuret-containing anion exchanger under conditions sufficient to increase the biuret content of said extract.

24. The method defined in claim 23 wherein said aqueous extractant has a pH of about 7 or less and is contacted with a biuret-containing anion exchanger for a total of at least three cycles and at a temperature sufficient to increase the biuret content of said extract to at least about 4 weight percent.

25. The method defined in claim 23 wherein said aqueous extractant is contacted with a biuret-containing anion exchanger at a pH of about 7 or less and a temperature of at least about 50° C. for a total of at least 3 cycles sufficient to increase the biuret content of said extract to at least about 10 weight percent.

26. The method defined in claim 24 which further comprises the step of recovering at least a portion of the biuret from said extract.

27. The method defined in claim 26 wherein the resulting extract of reduced biuret content is contacted with a biuret-containing ion exchanger under conditions sufficient to remove at least a portion of said biuret from said ion exchanger.

28. The method defined in claim 24 which further comprises the step of cooling said extract to a temperature sufficient to crystallize at least a portion of said biuret from said extract.

29. A method for producing biuret which comprises heating urea at a temperature sufficient to convert at least a portion of said urea to form a mixture comprising at least about 5 weight percent biuret and higher molecular weight urea condensation products, contacting an aqueous solution comprising said mixture with the hydroxide ion form of an anion exchanger under conditions sufficient to retain at least a portion of said biuret on said anion exchanger, and contacting the resulting biuret-containing anion exchanger with an aqueous extractant under conditions sufficient to form an extract comprising biuret in which the relative proportion of said higher molecular weight products to said biuret is less than said relative proportion in said aqueous solution.

30. The method defined in claim 29 wherein said urea is heated at a temperature of at least about 135° C. and said biuret-containing aqueous extract has a pH of about 7 or less.

31. The method defined in claim 29 wherein said aqueous extractant has a pH of about 7 or less and is contacted with said biuret-containing anion exchanger at a temperature of at least about 30° C.

* * * * *